(12) United States Patent
Delaney et al.

(10) Patent No.: US 7,306,786 B2
(45) Date of Patent: Dec. 11, 2007

(54) CALCIUM PHOSPHATE CEMENTS COMPRISING A WATER-SOLUBLE CONTRAST AGENT

(75) Inventors: David Delaney, Scotts Valley, CA (US); Brent Constantz, Cupertino, CA (US)

(73) Assignee: Skeletal Kinetics, LLC, Cupertino, CA (US)

( * ) Notice: Subject to any disclaimer, the term of this patent is extended or adjusted under 35 U.S.C. 154(b) by 374 days.

(21) Appl. No.: 10/629,321

(22) Filed: Jul. 28, 2003

(65) Prior Publication Data

US 2005/0023171 A1  Feb. 3, 2005

(51) Int. Cl.
A61K 49/04 (2006.01)
(52) U.S. Cl. .................. 424/9.41; 424/1.11; 424/1.65; 424/1.37; 424/9.4
(58) Field of Classification Search ............... 424/1.11, 424/1.29, 1.37, 1.61, 1.65, 9.1, 9.4, 9.41
See application file for complete search history.

(56) References Cited

U.S. PATENT DOCUMENTS

| | | | |
|---|---|---|---|
| 4,160,012 A | 7/1979 | Ono et al. | |
| 4,161,511 A | 7/1979 | Shiraki et al. | |
| 4,429,691 A | 2/1984 | Niwa et al. | |
| 4,497,075 A | 2/1985 | Niwa et al. | |
| 4,990,163 A | 2/1991 | Ducheyne et al. | |
| 5,129,905 A | 7/1992 | Constantz | |
| 5,266,534 A | 11/1993 | Atsumi et al. | |
| 5,281,265 A | 1/1994 | Liu | |
| 5,525,148 A | 6/1996 | Chow et al. | |
| 5,545,254 A | 8/1996 | Chow et al. | |
| 5,580,623 A | 12/1996 | Fulmer et al. | |
| 5,605,713 A | 2/1997 | Boltong | |
| 5,648,097 A | 7/1997 | Nuwayser | |
| 5,660,624 A | 8/1997 | Dry | |
| 5,679,294 A | 10/1997 | Umezu et al. | |
| 5,680,623 A | 10/1997 | Onuma | |
| 5,695,729 A | 12/1997 | Chow et al. | |
| 5,697,981 A | 12/1997 | Ison et al. | |
| 5,891,233 A | 4/1999 | Salonen et al. | |
| 5,900,254 A | 5/1999 | Constantz | |
| 5,954,867 A | 9/1999 | Chow et al. | |
| 5,962,028 A | 10/1999 | Constantz | |
| 5,968,253 A | 10/1999 | Poser et al. | |
| 5,976,234 A | 11/1999 | Chow et al. | |
| 5,997,624 A | 12/1999 | Chow et al. | |
| 6,005,162 A | 12/1999 | Constantz | |
| 6,027,742 A | 2/2000 | Lee et al. | |
| 6,139,578 A | 10/2000 | Lee et al. | |
| 6,201,039 B1 | 3/2001 | Brown et al. | |
| 6,273,916 B1 | 8/2001 | Murphy | |
| 6,309,420 B1 | 10/2001 | Preissman | |
| 6,312,468 B1 | 11/2001 | Best et al. | |
| 6,323,146 B1 | 11/2001 | Pugh et al. | |
| 6,334,891 B1 * | 1/2002 | Constantz et al. ............. 106/35 |
| 6,375,935 B1 * | 4/2002 | Constantz .................... 424/57 |
| 6,379,453 B1 | 4/2002 | Lin et al. | |
| 6,398,859 B1 | 6/2002 | Dickens et al. | |
| 6,451,059 B1 | 9/2002 | Janas et al. | |
| 6,458,423 B1 | 10/2002 | Goodson | |
| 6,461,632 B1 | 10/2002 | Gogolewski | |
| 6,488,667 B1 | 12/2002 | Murphy | |
| 6,518,212 B1 | 2/2003 | Wagh et al. | |
| 6,719,993 B2 * | 4/2004 | Constantz .................... 424/423 |
| 2002/0155187 A1 | 10/2002 | Lee et al. | |
| 2003/0021824 A1 | 1/2003 | Lacout et al. | |
| 2003/0049329 A1 | 3/2003 | Lee et al. | |
| 2003/0198615 A1 | 10/2003 | Chaput et al. | |
| 2004/0076585 A1 | 4/2004 | Tas | |

FOREIGN PATENT DOCUMENTS

WO 2004/050131 * 6/2004

OTHER PUBLICATIONS

The Merck Index, 1989, 11fth edition, p. 1011.*

* cited by examiner

*Primary Examiner*—Dameron L. Jones
(74) *Attorney, Agent, or Firm*—Bret E. Field; Bozicevic, Field & Francis LLP

(57) ABSTRACT

Methods are provided for producing flowable compositions, e.g. pastes, that set into calcium phosphate products and include a contrast agent. In the subject methods, dry reactants that include a calcium source and a phosphate source are combined with setting fluid and a water-soluble contrast agent, e.g., a water-soluble barium salt, and the combined reactants are mixed to produce the flowable composition. Also provided are the compositions themselves as well as kits for preparing the same. The subject methods and compositions produced thereby find use in a variety of applications, including the repair of hard tissue defects, e.g., bone defects.

27 Claims, No Drawings

CALCIUM PHOSPHATE CEMENTS COMPRISING A WATER-SOLUBLE CONTRAST AGENT

FIELD OF THE INVENTION

The field of this invention is calcium phosphate cements.

BACKGROUND

Calcium phosphate cements that are prepared by combining a dry component(s) and a liquid to form a flowable paste-like material that is subsequently capable of setting into a solid calcium phosphate product hold great promise for use as structural materials in the orthopedic and dental fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are susceptible to remodeling, making such products extremely attractive for use in orthopedics and related fields.

While a large number of different calcium phosphate cement formulations have been developed, there is a continued need for the development of yet more advanced formulations. Of particular interest is the development of formulations that include a contrast agent to aid in imaging of the cement during implantation.

Relevant Literature

United States patents of interest include: U.S. Pat. Nos. 6,375,935; 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; 4,429,691; 4,161,511 and 4,160,012.

Additional U.S. patents of interest include: U.S. Pat. Nos. 5,129,905; 6,273,916; 6,309,420; and 6,488,667.

SUMMARY OF THE INVENTION

Methods are provided for producing flowable compositions, e.g. pastes, that set into calcium phosphate products and include a water-soluble contrast agent. In the subject methods, dry reactants that include a calcium source and a phosphate source are combined with a setting fluid and a water-soluble contrast agent, e.g., a water-soluble barium salt, and the combined reactants are mixed to produce the flowable composition. Also provided are the compositions themselves as well as kits for preparing the same. The subject methods and compositions produced thereby find use in a variety of applications, including hard tissue repair applications, such as vertebroplasty applications.

DESCRIPTION OF THE SPECIFIC EMBODIMENTS

Methods are provided for producing flowable compositions, e.g. pastes, that set into calcium phosphate products and include a contrast agent. In the subject methods, dry reactants that include a calcium source and a phosphate source are combined with setting fluid and a water-soluble contrast agent, e.g., a water-soluble barium salt, and the combined reactants are mixed to produce the flowable composition. Also provided are the compositions themselves as well as kits for preparing the same. The subject methods and compositions produced thereby find use in a variety of applications, including the repair of hard tissue defects, such as vertebroplasty applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

In further describing the subject invention, the subject methods will be described first, followed by a description of the compositions produced thereby, kits for use in preparing the same and methods for using the subject compositions in methods of hard tissue, e.g. bone repair.

Methods

In the subject methods, dry reactants that include a calcium source and a phosphate source are combined with a setting fluid and a water-soluble contrast agent under conditions sufficient to produce a settable, e.g., flowable, composition that includes the water-soluble contrast agent and sets into a calcium-phosphate containing product, even when immersed in a fluid environment.

In the subject methods, the dry reactants include a calcium source and a phosphate source. The dry reactants are typically particulate compositions, e.g., powders, where the particle size of the components of the particulate compositions typically ranges from about 1 to about 1000 microns, usually from about 1 to about 200 microns and more usually from about 1 to about 40 microns.

As mentioned above, the dry reactants include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2 \cdot H_2O$); DCPD (dicalcium phosphate dihydrate, brushite or $CaHPO_4 \cdot 2H_2O$), ACP (amorphous calcium phosphate or $Ca_3(PO_4)_2 H_2O$), DCP (dicalcium phosphate, monetite or $CaHPO_4$), tricalcium phosphate, including both α- and β-$(Ca_3(PO_4)_2$, tetracalcium phosphate $(Ca_4(PO_4)_2O$, etc. Calcium sources of interest include, but are not limited to: calcium carbonate ($CaCO_3$), calcium oxide (CaO), calcium hydroxide ($Ca(OH)_2$) and the like. Phosphate sources of interest include, but are not limited to: Phosphoric acid ($H_3PO_4$), all soluble phosphates, and the like.

A variety of calcium phosphate cement compositions are known to those of skill in the art, and such cements may be readily modified into cements of the subject invention by including a water-soluble contrast agent, as described below. Cement compositions known to those of skill in the art and of interest include, but are not limited to, those described in U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from about 4:1 to 0.5:1, usually from about 2:1 to 1:1 and more usually from about 1.9:1 to 1.33:1.

The second component of the subject cement compositions is a setting fluid, as summarized above. The setting fluid can be any of a variety of setting fluids known to those of skill in the art. Setting fluids include a variety of physiologically compatible fluids, including, but are not limited to: water (including purified forms thereof), aqueous alkanol solutions, e.g. glycerol, where the alkanol is present in minor amounts, preferably less than about 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of about 0.01 to about 2M, such as from about 0.05 to about 0.5M, and at a pH in the range of about 6 to about 11, such as from about 7 to about 9, including from about 7 to about 7.5; and the like.

Of particular interest in certain embodiments is a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0-0.1 to 20%, usually from about 0.01-5 to 15% and more usually from about 5 to 10%.

Representative silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755-761.

In certain embodiments, the solution may further include an amount of phosphate ion, as described in U.S. application Ser. No. 10/462,075; the disclosure of which is herein incorporated by reference.

As summarized above, a feature of the subject cement compositions is that they further include a water-soluble contrast agent. By water-soluble contrast agent is meant an agent that readily dissolves in water (i.e., is water-soluble), as defined above. In many embodiments, the water-soluble contrast agent is a water-soluble salt of a radio-opaque element, i.e., an element that is visible under standard imaging techniques and protocols employed by those of skill in the art, e.g., fluoroscopic X-ray imaging protocols, etc. The radio-opaque element is one that appears different from calcium when viewed using such imaging techniques, where representative elements of interest include, but are not limited to: barium, oxalate, zirconium, tantalum, tungsten and the like. In certain embodiments, the contrast agent is a salt of an element that is incorporated into a compound of the calcium phosphate product of the flowable composition produced by the cement. For example, in certain embodiments the salt is a salt of an element that is incorporated into an apatitic compound present in the calcium phosphate product. Of particular interest are water-soluble barium salts, e.g., barium halides, including barium chloride, etc.

The water-soluble contrast agent as described above may be initially present as a component separate from the dry reactants and setting fluid components, or combined with one or both of these initially disparate components, such that it may be present in the dry reactants and/or setting fluid when the dry reactants and setting fluid are combined, as described below.

One or both of the above liquid and dry reactant components may include an active agent that modulates the properties of the product into which the flowable composition prepared by the subject method sets. Such additional ingredients or agents include, but are not limited to: organic polymers, e.g., proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include, but are not limited to: osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g., NaCl, calcium sulfate; sugars, e.g., sucrose, fructose and glucose; pharmaceutically active agents, e.g., antibiotics; and the like In practicing the subject methods, suitable amounts of the dry reactants, the setting fluid and the water-soluble contrast agent are combined to produce a settable or flowable composition. In other words, the ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In many embodiments, the liquid to solids ratio is chosen to provide for a flowable composition that has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45.

The amount of water-soluble contrast agent that is combined with the dry and liquid components, described above, is sufficiently great to provide for the desired amount of contrast during imaging yet sufficiently small such that there is little if any excess agent available following production of the calcium phosphate product that can move beyond the site of implantation, e.g., and systemically contact the host. In certain embodiments, the amount of contrast agent ranges in from about 1 to about 50% by weight, such as from about 5 to about 40% by weight, including from about 10 to about 35% by weight.

As mentioned above, the requisite amounts of dry reactants, setting fluid and water-soluble contrast agent (which may be separate from or present in one or both of the dry reactants and setting fluid) are combined under conditions sufficient to produce the flowable product composition. As such, the dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference.

In certain embodiments, a simple cylindrical tube may be used both as a storage and packaging device and a mixing and delivery device. The plastic tube or analogous containment structure is separated into at least two sections, compartments or portions. One section or portion contains the powder component, as described above. The at least one more compartment contains the setting fluid, where in certain embodiments, two or more compartments for setting fluid components are provided, e.g., where it is desired to keep the disparate components of the setting fluid separate prior to use, and/or where one desires to have flexibility in determining the amounts of the phosphate and silicate ions in the setting fluid that is employed. For example, one may have a two-compartment device with powder in one component and a setting fluid in the other. In other embodiments, one may have a three compartment device, with powder in a first compartment, silicate solution in a second compartment and phosphate solution in a third compartment. In yet other embodiments, one may have a multi-compartment device, with powder in a first compartment, a solution at one concentration of either or both component ions in a second compartment, and a solution at a second concentration of either or both component ions in a third compartment, etc., where this type of embodiment allows one to "tailor" the setting fluid employed depending on the particular application in which the cement is to be used. In yet other embodiments, one may have a three-compartment device with powder in the middle component and setting solution in the two outer components, where each setting solution may be the same or different. Additional compartments may be present for additional components as desired, e.g., water-soluble contrast agent, cement modifiers, etc.

The two or more compartments are separated from each other by an easily removable barrier that can be readily removed during preparation of the packaged cement. Any convenient removable barrier may be present in the device, where a representative barrier means of interest is a dialysis bag clip or analogous means. Another representative barrier means of interest is a frangible barrier, as described in WO 98/28068 and U.S. Pat. No. 5,362,654; the disclosures of which are herein incorporated by reference. When one is ready to mix, the clip or other barrier means between the areas (liquid(s) and powder) is removed (e.g., unclipped), and the contents are simply kneaded together by hand or other technique. The above steps may be performed through a second outer covering for sterility—i.e., the above-described package elements may be present in a second outer covering for sterility. The outer covering may then be removed and the mixed contents from the tube may be delivered from one end of the storage/mixing tube using a peristaltic action.

The above-described packaging may be further modified to include one or more additional components that are employed during use/delivery of the product composition, such as removable delivery elements, elements for transferring the product cement into an attached delivery element, elements that assist in combining the components to produce the desired product composition, etc.

The temperature of the environment in which combination or mixing of the dry and liquid components takes place is sufficient to provide for a product that has desired setting and strength characteristics, and typically ranges from about 0 to 50° C., usually from about 20 to 30° C. Mixing takes place for a period of time sufficient for the flowable composition to be produced, and generally takes place for a period of time ranging from about 15 to 100 seconds, usually from about 15 to 50 seconds and more usually from about 15 to 30 second.

The above-described protocols result in a flowable composition that is capable of setting into a calcium phosphate mineral product, as described in greater detail below, where the flowable composition is radioopaque during, at least during implantation.

Settable/Flowable Compositions

The flowable compositions produced by the above-described methods are radio-opaque compositions that set into a biologically compatible, and often resorbable and/or remodelable, product, where the product is characterized by including calcium phosphate molecules not present in the initial reactants, i.e., that are the product of a chemical reaction among the initial reactants, where in many embodiments at least a portion of the product calcium phosphate molecules include radioopaque atoms other than calcium atoms, e.g., barium atoms.

The term flowable is meant to include paste-like compositions, as well as more liquid compositions. As such, the viscosity time of the subject flowable compositions, defined as time periods under which the mixed composition injects through a standard Luer-lok fitting after mixing, typically ranges up to about 10 minutes, usually up to about 7 minutes, such as up to about 4 minutes. Of particular interest in many embodiments are paste compositions that have an injectable viscosity that injects in a time period ranging up to about 5 minutes, such as about up to about 4 minutes. Pastes that stay paste-like for longer period may be displaced by bleeding bone once inplanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically ranges from about 2:1 to 1.33:1, usually from about 1.8:1 to 1.5:1 and more usually from about 1:7:1 to 1.6:1. Of particular interest in many embodiments are apatitic products, which apatitic products have a calcium to phosphate ratio ranging from about 2.0:1 to 1.33:1, including both hydroxyapatite and calcium deficient analogs thereof, including carbonate substituted hydroxyapatite (i.e. dahllite), etc. The subject paste-like composition is, in many embodiments, one that is capable of setting into a hydroxyapatitic product, such as a carbonated hydroxyapatite, i.e. dahilite, having a carbonate substitution of from about 2 to about 10%, usually from about 2 to about 8% by weight of the final product.

The period of time required for the compositions to harden or "set" may vary. By set is meant: the Gilmore Needle Test (ASTM C266-89), modified with the cement submerged under 37° C. physiological saline. The set times of the subject cements may range from about 30 seconds to 30 minutes, and will usually range from about 2 to 15 minutes and more usually from about 4 to 12 minutes. In many embodiments, the flowable composition sets in a clinically relevant period of time. By clinically relevant period of time is meant that the paste-like composition sets in less than about 20 minutes, usually less than about 15 minutes and often in less than about 10 minutes, where the composition remains flowable for at least about 1 minute, usually at least about 2 minutes and, in many embodiments, for at least about 5 minutes following combination or mixture of the precursor liquid and dry cement components.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 20, usually at least about 40 and more usually at least about 50 MPa, as measured by the assay described in Morgan, EF et al., 1997, Mechanical Properties of Carbonated Apatite Bone Mineral Substitute: Strength, Fracture and Fatigue Behavior. J. Materials Science: Materials in Medicine. V. 8, pp 559-570., where the compressive strength of the final apatitic product may be as high as 60 MPa or higher. Inclusion of the silicate in the setting liquid allows lower liquid to solids ratios to be employed which results in significantly higher compressive strengths. Compressive strengths can be obtained that range as high 100 to 200 MPa. In certain embodiments, the resultant product has a tensile strength of at least about 0.5 MPa, such as at least about 1 MPa, including at least about 5 MPa, at least about 10 MPa or more, e.g., from about 0.5 to about 10 MPa, as determined by the tensile strength assay appearing in the Experimental Section, below.

In many embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for at least about 4 months, at least about 6 months, at least about 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for at least about 4 months, at least about 6 months, at least about 1 year or longer, e.g., 2.5 years, 5 years, etc.

In many embodiments, the flowable paste-like composition is capable of setting in a fluid environment, such as an in vivo environment at a bone repair site. As such, the flowable paste composition can set in a wet environment, e.g., one that is filled with blood and other physiological fluids. Therefore, the site to which the flowable composition is administered during use need not be maintained in a dry state.

In certain embodiments, the subject cement compositions may be seeded with any of a variety of cells, as described in published U.S. patent application Ser. No. 20020098245, the disclosure of which is herein incorporated by reference.

In addition, in certain embodiments the compositions include demineralized bone matrix, which may be obtained typically in a lyophilized or gel form and is combined with the cement composition at some prior to implantation. A variety of demineralized bone matrixes are known to those of skill in the art and any convenient/suitable matrix composition may be employed.

In certain embodiments, the cements may include one or more collections of contrast particles (for example, for use as tracers during use of the cement), e.g., as described in U.S. Pat. No. 6,273,916; the disclosure of which is herein incorporated by reference.

Applications

The subject methods and compositions produced thereby, as described above, find use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone.

One particular application in which the subject compositions find use is vertebroplasty, particularly percutaneous vertebroplasty. Percutaneous vertebroplasty is a well-known procedure involving the injection of a bone cement or suitable biomaterial into a vertebral body via percutaneous route under imaging guidance, such as X-ray guidance, typically lateral projection fluoroscopy. The cement is injected as a semi-liquid substance through a needle that has been passed into the vertebral body, generally along a transpedicular or posterolateral approach. The three main indications are benign osteoporotic fractures, malignant metastatic disease and benign tumors of the bone. Percutaneous vertebroplasty is intended to provide structural reinforcement of a vertebral body through injection, by a minimally invasive percutaneous approach, of bone cement into the vertebral body. See, for example, Cotton A., et al "Percutaneous vertebroplasty: State of the Art." Radiograhics 1998 March-April; 18(2):311-20; discussion at 320-3.

The general steps for performing a vertebroplasty are as follows. The patient is placed in the prone position and the skin overlying the fractured vertebrae is prepped and draped. A suitable local anesthetic such as 1% Lidocaine is injected into the skin underlying fat and into the periosteum of the pedicle to be entered. Next, a skin incision of about five millimeters is made with a No. 11 scalpel blade or other suitable surgical implement. The decision regarding which pedicle to use is made based on CT (computed tomography) 10 and MR (magnetic resonance) images. A needle of an appropriate gauge (such as eleven gauge or thirteen gauge in a smaller vertebral body) is passed down the pedicle until it enters the vertebral body and reaches the junction of the anterior and middle thirds. This area is the region of maximum mechanical moment and usually the area of greatest compression. At this point a vertebrogram can be performed, if desired, by the injection of non-ionic X-ray contrast into the vertebral body to look for epidural draining veins.

Next, a cement is prepared, e.g., according to the methods as described above. The cement is then injected under lateral X-Ray projection fluoroscopy imaging or other suitable imaging. The posterior aspect of the vertebral body is an important area to observe for posterior extension of cement, and it is generally accepted that this should be watched constantly during the injection. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved. On average, about four to five cubic-centimeters of cement can be injected on each side, and it is known to inject up to about eight to nine cubic-centimeters per side.

Other orthopedic applications in which the cements prepared by the subject system find particular use include the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in U.S. Pat. No. 6,149,655, the disclosure of which is herein incorporated by reference. In addition to these particular applications described in this U.S. patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference.

Kits

Also provided are kits comprising the subject cements, where the dry and liquid components may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference. In certain embodiments, the kits may include two or more setting fluids in different concentrations, e.g., where one wishes to provide a kit with flexibility with respect to the nature of the setting fluid that is prepared therefrom. For example, a kit may include two more different phosphate-silicate solutions that differ from each other with respect to their silicate and/or phosphate components. Alternatively, the kit may include to or more different, separate phosphate and/or silicate solutions that differ from each other in terms of concentration and that are mixed upon use of the kit as desired to obtain a desired setting fluid. As mentioned above, the kit components may be present in separate containers. Alternatively, the components may be present as a packaged element, such as those described above.

In addition to the cement compositions, the subject kits may further include a number of additional reagents, e.g., cells (as described above, where the composition is to be seeded), protein reagents (as described above), and the like.

In certain embodiments, the subject cements may be kitted as described in U.S. Pat. No. 6,273,916, the disclosure of which is herein incorporated by reference, e.g., packaged in a kit with at least two different sterilized pouches (or analogous compartments) of cement that may independently used at the same or different times, where each pouch may include the same or different cement formulation, e.g., where the cements may differ in terms of contrast characteristics.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Three different calcium phosphate cements were formulated by addition of barium chloride and/or barium carbonate (two soluble barium salts) to a basic cement formula containing $CaHPO_4$ (DCPA, 2.66 g) and $Ca_3(PO_4)_2$ (Alpha Tricalcium phosphate 6.20 g). The three different cement formulations were as follows:

1. Cement formula 1 contained 35% barium by weight. The Calcium plus Barium to phosphate molar ratio was 1.67. (Ca+Ba/PO$_4$)
2. Cement formula 2 contained 22% barium by weight. The Calcium plus Barium to phosphate molar ratio was 1.50. (Ca+Ba/PO$_4$)
3. Cement formula 3 contained 12% barium by weight. The Calcium plus Barium to phosphate molar ratio was 1.40. (Ca+Ba/PO$_4$)

2% sodium silicate solution was added to each of the above cement formulations to make a paste and plastic washers were filled with the resultant past to make specimens for clinical x-ray. Increasing radioopacity was observed with increasing barium content.

It is evident from the above results and discussion that calcium phosphate cements that are readily viewable under X-ray imaging technologies are provided. Benefits of the subject cements include extremely low toxicity, as the contrast element employed in the subject methods is rapidly incorporated into the calcium phosphate product of the subject cements, thereby minimizing systemic exposure of the host to the contrast agent. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of producing a flowable composition that sets into a calcium phosphate mineral product, said method comprising:
   (a) a setting fluid;
   (b) dry reactants comprising a calcium source and a phosphate source; and
   (c) a water-soluble contrast agent comprising a radio-opaque element other than calcium that is incorporated into said calcium phosphate product wherein said water-soluble contrast agent comprises a salt of a radio-opaque element;
   to produce said flowable material that sets into a calcium phosphate mineral product that includes atoms of said radio-opaque element incorporated into said mineral product.

2. The method according to claim 1, wherein said setting fluid comprises said water-soluble contrast agent.

3. The method according to claim 1, wherein said dry reactants comprise said water-soluble contrast agent.

4. The method according to claim 1 wherein said radio-opaque element is one that is incorporated into a calcium phosphate apatite structure of said calcium phosphate containing product.

5. The method according to claim 1 wherein said radio-opaque element is chosen from barium, oxalate, zirconium, tantalum and tungsten.

6. The method according to claim 5, wherein said radio-opaque element is barium.

7. The method according to claim 6, wherein said salt of said radio-opaque element is barium chloride.

8. The method according to claim 1, wherein said said dry reactant to setting fluid are combined in a ratio that ranges from about 0.2:1 to 0.7:1.

9. The method according to claim 8, wherein said flowable composition is a paste.

10. The method according to claim 1, wherein said setting fluid is a solution of a soluble silicate.

11. The method according to claim 1, wherein said flowable composition sets into said calcium phosphate containing product in a period of time ranging from about 5 to 10 minutes.

12. The method according to claim 1, wherein said calcium phosphate containing product has a compressive strength ranging from about 25 to 100 MPa.

13. A method of producing a paste that sets into a calcium phosphate mineral product, said method comprising:
   (a) combining:
      (i) dry reactants comprising a calcium source and a phosphate source
      (ii) a setting fluid; and
      (iii) a water-soluble barium salt; and
   (b) mixing said combined reactants and setting fluid to produce a paste that sets into a calcium phosphate mineral product.

14. The method according to claim 13, wherein said setting fluid comprises said water-soluble barium salt.

15. The method according to claim 13, wherein said dry reactants comprise said water-soluble barium salt.

16. The method according to claim 13, wherein said water-soluble barium salt is barium chloride.

17. The method according to claim 13, wherein said setting fluid is a solution of a soluble silicate.

18. The method according to claim 13, wherein both said setting fluid and dry reactants comprise said water-soluble barium salt.

19. The method according to claim 13, wherein said flowable composition sets into said calcium phosphate containing product in a period of time ranging from about 5 to 10 minutes.

20. The method according to claim 13, wherein said calcium phosphate containing product has a compressive strength ranging from about 25 to 100 MPa.

21. A flowable composition that sets into a calcium phosphate containing product, wherein said composition is produced by the method according to claim 1.

22. A kit for use in preparing a flowable composition that sets in an in vivo fluid environment into a calcium phosphate mineral product comprising calcium phosphate molecules, said kit comprising:
   (a) dry reactants comprising a calcium source and a phosphate source;
   (b) a setting fluid or components for producing the same; and
   (c) a water-soluble contrast agent comprising a radio-opaque element other than calcium that is incorporated into said calcium phosphate mineral product, wherein said calcium phosphate mineral product includes atoms of said radio-opaque element incorporated into said mineral product.

23. A packaged calcium phosphate cement, said packaged cement comprising:
   a tubular element separated into a first compartment and at least one additional compartment by a removable barrier;
      (i) dry reactants comprising a source of calcium and phosphate present in said first compartment;

(ii) a setting fluid or components thereof present in said at least one additional compartment; and (iii) a water-soluble contrast comprising a radio-opaque element other than calcium that is incorporated into a calcium phosphate mineral product, wherein said water-soluble contrast agent comprises a salt of a radio-opaque element, wherein said calcium phosphate mineral product includes atoms of said radio-opaque element incorporated into said mineral product, wherein said calcium phosphate mineral product is produced upon combination of said dry reactants and setting fluid, wherein said water-soluble contrast agent is present in either said first compartment, said at least one additional compartment or in a second additional compartment.

24. The packaged calcium phosphate cement according to claim 23, wherein said removable barrier is a clip.

25. The packaged calcium phosphate cement according to claim 23, wherein said removable barrier is a frangible barrier.

26. The method according to claim 23, wherein said setting fluid is a solution of a soluble silicate.

27. The method according to claim 1, wherein said contrast agent is present in an amount ranging from about 10 to abut 35% by weight.

* * * * *

UNITED STATES PATENT AND TRADEMARK OFFICE
CERTIFICATE OF CORRECTION

| | | |
|---|---|---|
| PATENT NO. | : 7,306,786 B2 | Page 1 of 1 |
| APPLICATION NO. | : 10/629321 | |
| DATED | : December 11, 2007 | |
| INVENTOR(S) | : David Delaney et al. | |

It is certified that error appears in the above-identified patent and that said Letters Patent is hereby corrected as shown below:

In Column 11, line 40, after the word "comprising" insert an additional line and insert the following word:

--combining:--

Signed and Sealed this

Third Day of March, 2009

JOHN DOLL
*Acting Director of the United States Patent and Trademark Office*